United States Patent
Aikawa et al.

(10) Patent No.: US 8,379,081 B2
(45) Date of Patent: Feb. 19, 2013

(54) APPEARANCE INSPECTION APPARATUS AND APPEARANCE INSPECTION METHOD

(75) Inventors: Tetsuro Aikawa, Tokyo (JP); Yoshinori Satoh, Tokyo (JP); Makoto Ochiai, Tokyo (JP); Hiroyuki Adachi, Tokyo (JP)

(73) Assignee: Kabushiki Kaisha Toshiba, Tokyo (JP)

(*) Notice: Subject to any disclaimer, the term of this patent is extended or adjusted under 35 U.S.C. 154(b) by 612 days.

(21) Appl. No.: 12/595,981

(22) PCT Filed: Apr. 24, 2008

(86) PCT No.: PCT/JP2008/057927
§ 371 (c)(1),
(2), (4) Date: Oct. 15, 2009

(87) PCT Pub. No.: WO2008/136348
PCT Pub. Date: Nov. 13, 2008

(65) Prior Publication Data
US 2010/0129059 A1    May 27, 2010

(30) Foreign Application Priority Data
Apr. 27, 2007 (JP) .............................. 2007-118541

(51) Int. Cl.
*H04N 3/00* (2006.01)
(52) U.S. Cl. ............................ 348/92; 375/240.17
(58) Field of Classification Search ............. 348/92
See application file for complete search history.

(56) References Cited

U.S. PATENT DOCUMENTS

| | | | | |
|---|---|---|---|---|
| 5,058,177 A | * | 10/1991 | Chemaly | 382/149 |
| 5,909,521 A | * | 6/1999 | Nakao et al. | 382/312 |
| 6,236,747 B1 | * | 5/2001 | King et al. | 382/149 |
| 6,456,318 B1 | * | 9/2002 | Noguchi | 348/87 |
| 2010/0309308 A1 | * | 12/2010 | Saphier et al. | 348/92 |

FOREIGN PATENT DOCUMENTS

| | | |
|---|---|---|
| JP | 3 214978 | 9/1991 |
| JP | 4 154292 | 5/1992 |
| JP | 5 240805 | 9/1993 |
| JP | 9 218941 | 8/1997 |
| JP | 2000 346976 | 12/2000 |
| JP | 2003 187223 | 7/2003 |
| JP | 2007 333639 | 12/2007 |

* cited by examiner

*Primary Examiner* — David Czekaj
*Assistant Examiner* — David N Werner
(74) *Attorney, Agent, or Firm* — Oblon, Spivak, McClelland, Maier & Neustadt, L.L.P.

(57) ABSTRACT

Visibility of defects is improved for inspection of structures and the like, by generating an image having higher resolution than pixel resolution of a TV camera itself. An appearance inspection apparatus is provided with a TV camera; a camera driving device for making the TV camera scan an inspection object; an image capture device for capturing the image in the TV camera as a digital image; a camera motion measuring device for measuring scanning motion of the TV camera; a high definition image generating device, which generates a high definition image having a higher pixel resolution than that of the TV camera, based on the digital images captured by the image capture device and the TV camera scanning motion data measured by the camera motion measuring device; and a recording device which records and stores positional information of the inspection object.

14 Claims, 7 Drawing Sheets

APPEARANCE INSPECTION APPARATUS AND APPEARANCE INSPECTION METHOD

TECHNICAL FIELD

The present invention relates to an appearance inspection apparatus and an appearance inspection method that use a TV camera.

BACKGROUND ART

Nuclear power plants are periodically inspected for the sake of maintaining safety and reliability of the plant structures and various devices. In particular, reactor internal structures are often inspected by indirect visual inspection using an underwater TV (television) camera or a TV camera accommodated in a watertight case. Among conventional examples of such an in-core visual inspection apparatus using an underwater TV camera is disclosed in Patent Document 1.

The inspection method disclosed in Patent Document 1 is to immerse a remote-controllable TV camera into the reactor to shoot an inspection object, and the human inspector visually checks the picture of the TV camera which is output on a monitor. Simultaneously with the inspector's visual observation, the moving picture is recorded on video tapes, optical disks, or the like. If any defect is found in the inspection object, the inspector checks the recorded picture to create an inspection record on the defect.

PATENT DOCUMENT 1: Japanese Patent Application Laid-Open Publication No. 2000-346976
PATENT DOCUMENT 2: Japanese Patent Application Laid-Open Publication No. H 03-214978
PATENT DOCUMENT 3: Japanese Patent Application Laid-Open Publication No. H 04-154292

DISCLOSURE OF THE INVENTION

Problems to be Solved by the Invention

When large-sized equipment such as a reactor internal structure is inspected by the foregoing inspection method, the image data in a TV camera on a plurality of locations or a wide area of the inspection object is recorded on video tapes or the like. The amount of data can be as enormous as several to several tens of video tapes etc. The inspectors who review the picture then need to search a plurality of video tapes for a picture that records the location to be checked. There is thus a problem of poor working efficiency, requiring inspection man-hours.

With the progress of data digitization in recent years, it has been attempted to record and store the picture into an optical disk or the like as a digital picture. Since the picture has an enormous amount of data, the picture data needs to be compressed by MPEG (Moving Picture Expert Group) or other methods. However, the picture compression methods that are currently prevalent are non-geometric, and thus cause degradation in information. In other words, there has been the problem that the compressed picture does not have brightness levels same as those of the picture yet to be compressed.

To be specific, MPEG compresses image data in units of local blocks inside, and thus produces block noise. Since the picture is intended for inspection, there has been the problem that the compression of the image data with image degradation can lower the inspection quality.

Representative still images alone may be recorded and stored. Replacing the information on the moving picture with still images selected from the moving picture, however, has had the problem that the decreased amount of information lowers the inspection quality as with the foregoing.

The indirect visual inspection using TV cameras has also had the problem that small defects are difficult to be discovered and can possibly be missed if the TV camera does not have a sufficient pixel resolution with respect to the defects to be detected.

Patent Documents 2 and 3 disclose technologies of moving an imaging device such as a TV camera by only a small amount to improve the substantial resolution by using the image data before and after the movement. However, since the technologies disclosed in these documents handle the relative position between the imaging device and the object as known information, the casing of the TV camera is required to be fixed to the object. Scanning the object with the TV camera also requires a mechanism that moves the casing of the TV camera precisely with respect to the object.

The present invention has been achieved in view of the foregoing circumstances. It is thus an object thereof to provide an appearance inspection apparatus and an appearance inspection method that can generate a picture having a resolution higher than the pixel resolution of the TV camera itself to obtain an inspective image with improved defect visibility, and allow easily reviewing of the picture.

Means for Solving the Problem

In order to achieve the above-mentioned object, according to an aspect of the present invention, there is provided a appearance inspection apparatus comprising: an image capture unit that captures a picture of a TV camera as a digital image before and after the TV camera makes a relative scanning motion such that the TV camera moves relative to an inspection object; a camera motion measuring unit that measures the relative scanning motion of the TV camera; a high definition image generating unit that generates a high definition image having a pixel resolution higher than that of the TV camera based on a plurality of the digital images captured by the image capture unit and scanning motion data on the TV camera measured by the camera motion measuring unit; and a recording unit that records and stores position information on the inspection object.

According to another aspect of the present invention, there is provided an appearance inspection apparatus comprising: an image capture unit that captures a picture of a TV camera as a digital image before and after the TV camera makes a relative scanning motion such that the TV camera moves relative to an inspection object; a camera motion measuring unit that measures the relative scanning motion of the TV camera; a CAD recording unit that contains CAD data describing a shape of the inspection object; a high definition image generating unit that generates a high definition image having a pixel resolution higher than that of the TV camera based on a plurality of the digital images captured by the image capture unit and scanning motion data on the TV camera measured by the camera motion measuring unit; and a recording unit that records and stores position information on the inspection object.

According to yet another aspect of the present invention, there is provided an appearance inspection apparatus comprising: an image capture unit that captures a picture of a TV camera as a digital image before and after the TV camera makes a relative scanning motion such that the TV camera moves relative to an inspection object; a position measuring unit that measures scanning motion data on the TV camera based on a position and direction of the TV camera; a recording unit that records the data measured by the position measuring unit; a CAD recording unit that contains CAD data describing a shape of the inspection object; a high definition image generating unit that generates a high definition image having a pixel resolution higher than that of the TV camera based on a plurality of the digital images captured by the image capture unit and the scanning motion data; a developed view generating unit that generates a developed view in which the inspection object is developed in the plane; and a recording unit that records and stores position information on the inspection object.

According to yet another aspect of the present invention, there is provided an appearance inspection method comprising steps of shooting an inspection object with a TV camera while making the TV camera perform a relative scanning motion such that the TV camera moves relative to the inspection object; capturing a picture shot by the TV camera into an image capture unit as a digital image; measuring the scanning motion of the TV camera based on the image of the TV camera; generating a high definition image having a pixel resolution higher than that of the TV camera based on measurements of the scanning motion of the TV camera and the digital image captured into the image capture unit; displaying the high definition image; and recording and storing position information on the inspection object.

Advantages of the Invention

According to the present invention, a picture having a resolution higher than the pixel resolution of the TV camera itself can be generated to obtain an inspective image with improved defect visibility. In addition, the picture can be reviewed easily.

EXPLANATION OF REFERENCE SYMBOLS

100: inspection object
101: TV camera
102: camera driving device
104: camera motion measuring device
105: image capture device
106: high definition image generating device
107: display device
108: recording device
300: drive control device
301: CAD recording device
400: position measuring device
401: developed view generating device
500: image selection device
501: image enhancing device
600: image processing device
700: hanging tool

BEST MODE FOR CARRYING OUT THE INVENTION

Hereinafter, embodiments of the present invention will be described with reference to the drawings.

(First Embodiment)

Figure 1:
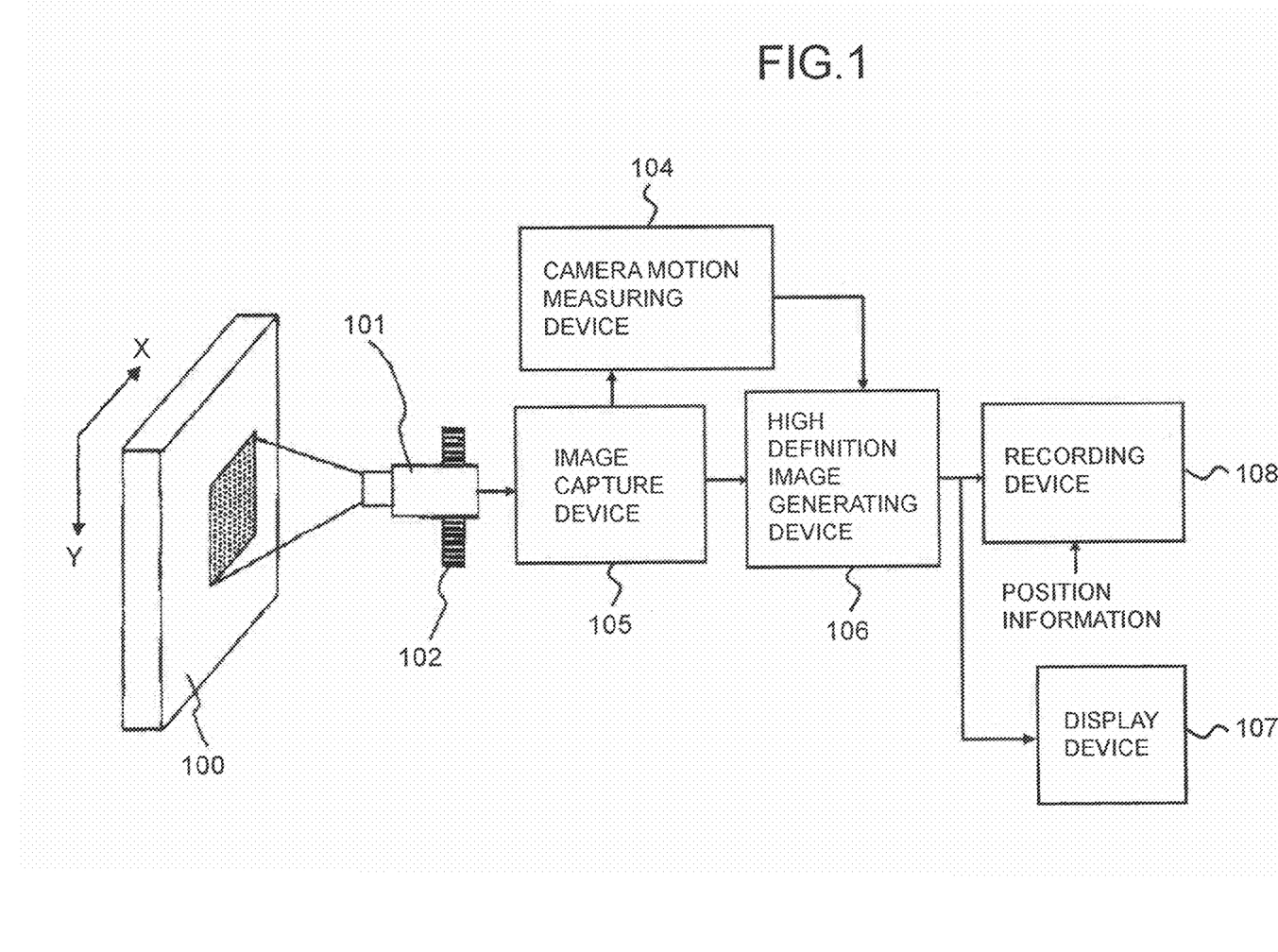
FIG. 1 is a block diagram of a visual inspection apparatus (appearance inspection apparatus) according to a first embodiment of the present invention.

FIG. 1 is a block diagram showing the configuration of a visual inspection apparatus (appearance inspection apparatus) according to a first embodiment of the present invention. An inspection object 100 may be a reactor pressure vessel or a reactor internal structure of a nuclear power plant such as a steam dryer, for example.

As shown in FIG. 1, the visual inspection apparatus according to the first embodiment includes: a TV camera 101 that shoots the inspection object 100; a camera driving device 102 on which the TV camera 101 is mounted for a scanning motion; an image capture device 105 that captures the picture of the TV camera 101 as a digital image; a camera motion measuring device 104 that measures the scanning motion of the TV camera 101; a high definition image generating device 106 that generates a high definition image having a pixel resolution higher than that of the TV camera 101; a display device 107 that displays the high definition image; and a recording device 108 that records the high definition image and position information of the inspection object 100 seen in the high definition image.

Next, the operation of the visual inspection apparatus according to the first embodiment will be described. The TV camera 101 shoots the inspection objects 100 while the camera driving device 102 makes the TV camera 101 perform a scanning motion finer than the pixels of the TV camera in two-dimensional X and Y directions with respect to the inspection object 100. The picture shot by the TV camera 101 is input to the image capture device 105 and captured as a digital image, which is transmitted to the camera motion measuring device 104 and the high definition image generating device 106.

The camera motion measuring device 104 has an image processing function. The camera motion measuring devices 104 records images transmitted from the image capture device 105 in succession, and compares a previous image recorded and the latest image transmitted from the image capture device 105 to measure the scanning motion of the TV camera 101 in the images with precisions of sub-pixels smaller than a single pixel. In an example of the measuring method, the images are magnified to increase the pixel precisions of the images, and brightness correlation-based block matching is performed between the two images to measure the scanning motion from the positions of highest brightness correlation pixel by pixel.

If the inspection object 100 has an uneven surface, the distance from the TV camera 101 to the inspection object 100 is not constant. The scanning motion therefore needs to be determined for each of the image pixels by block matching or other methods.

The high definition image generating device 106 generates a high definition image having a pixel resolution higher than that of the TV camera 101 from the images transmitted from the image capture device 105 and scanning motion data which is the result of measurement by the camera motion measuring device 104.

Figure 2:
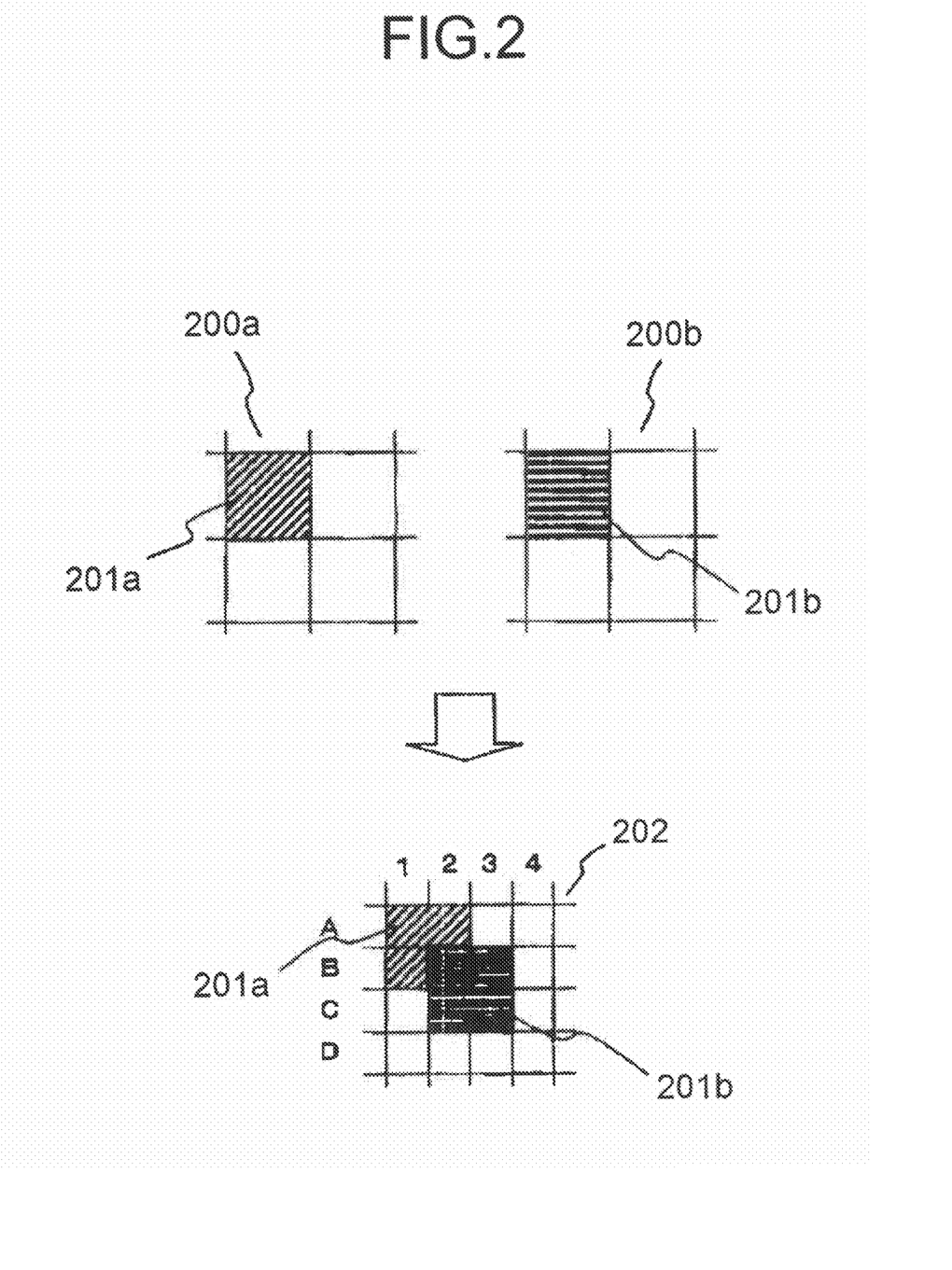
FIG. 2 is an explanatory diagram showing a method of generating a high definition image according to the first embodiment of the present invention.

FIG. 2 shows an example of the method of generating a high definition image. Two consecutive images 200a and 200*b* of the image capture device 105 are taken into the high definition image generating device 106. A high definition image 202 in this example is set at a pixel resolution twice that of the images 200*a* and 200*b*. Suppose that a pixel 201*a* of the image 200*a* corresponds to the pixels at coordinates 1A, 2A, 1B, and 2B of the high definition image 202. The relative position of a pixel 201*b* of the image 200*b* with respect to the image 200*a* is calculated from the scanning motion data of the camera motion measuring device 104, and the coordinates of the pixel 201*b* in the high definition image 202 are calculated. In this example, the coordinates shall be 2B, 3B, 2C, and 3C.

Next, the brightnesses of the high definition image 202 are calculated. In the example of FIG. 2, the coordinate 2B of the high definition image 202 is where the pixel 201*a* of the image 200*a* and the pixel 201*b* of the image 200*b* overlap each other. The brightness at the coordinates 2B of the high definition image 202 is estimated from the brightnesses of the pixel 201*a* and the pixel 201*b*. The brightness of each pixel of the high definition image 202 is thus estimated to generate a high definition image that has a pixel resolution higher than that of the TV camera.

The high definition image generated by the high definition image generating device 106 is displayed on the display device 107. The recording device 108 records and stores the high definition image generated by the high definition image generating device 106 along with the position information on the inspection object that is seen in the high definition image. When the position of the inspection object 100 is specified, the recording device 108 can refer to a past high definition image of that position. The high definition image referred to is displayed on the display device 107.

According to the first embodiment, high definition images having a pixel resolution higher than that of the TV camera 101 can be generated and displayed on the display device 107, whereby defect visibility is increased for improved inspection quality. Converting the moving picture of the TV camera 101 into high definition images, which are still images, can suppress degradation in image quality and image information and reduce the data capacity, allowing improved economical efficiency as a data-storing system. Since the high definition images are recorded and stored with the position information, the inspector can easily review the inspection images of desired positions.

(Second Embodiment)

Figure 3:
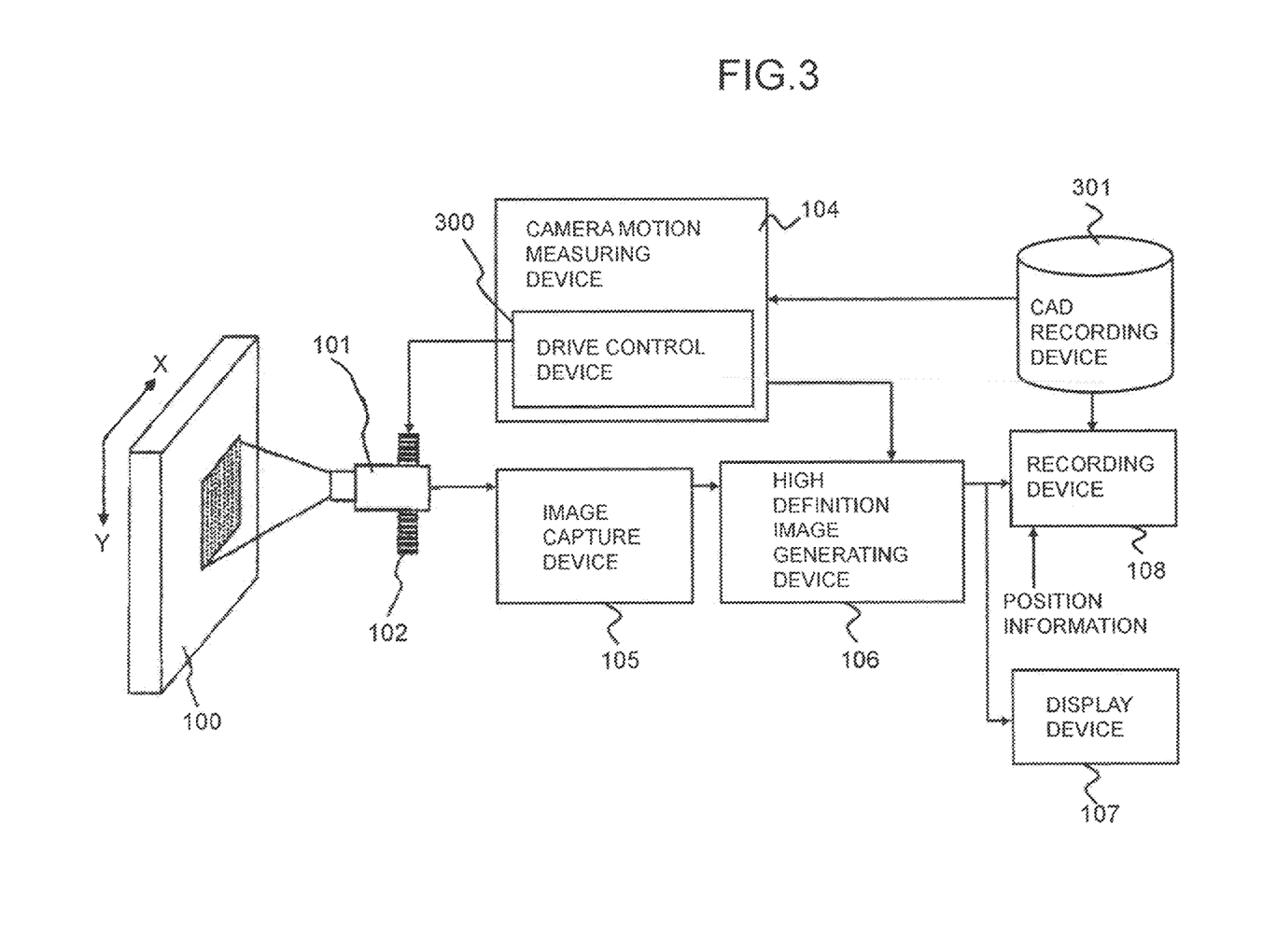
FIG. 3 is a block diagram of a visual inspection apparatus according to a second embodiment of the present invention.

FIG. 3 is a block diagram showing the configuration of a visual inspection apparatus according to a second embodiment of the present invention. In FIG. 3, identical or similar components to those of FIG. 1 will be designated by like reference numerals, and description thereof will be omitted. As compared to the first embodiment shown in FIG. 1, the second embodiment includes: a drive control device 300 which is added to the camera motion measuring device 104; and a CAD (Computer-Aided Design) recording device 301. The present embodiment is predicated on that there is recorded existing CAD data that describes the shape of the inspection object, such as when the inspection object is designed and produced by using CAD.

Next, the operation of the visual inspection apparatus according to the second embodiment will be described. The drive control device 300 controls the camera driving device 102 under predetermined settings or operator's operations so that the TV camera 101 makes a scanning motion. The CAD recording device 301 contains the CAD data that describes the shape of the inspection object. Based on control information of the drive control device 300 and the shape of the inspection object 100 recorded in the CAD recording device 301, the camera motion measuring device 104 measures the scanning motion of the TV camera 101 in the image with precisions of sub-pixels smaller than a single pixel, thereby obtaining scanning motion data. The recording device 108 records and stores the position of the inspection object 100 in terms of the coordinates on the CAD data recorded in the CAD recording device 301. When a position is specified on the CAD data, the recording device 108 can refer to a past high definition image of that position. The high definition image referred to is displayed on the display device 107 and presented to the inspector.

According to the second embodiment, the scanning motion of the TV camera 101 in the image is measured from the control information of the drive control device 300 and the shape of the inspection object 100 recorded in the CAD recording device 301. This eliminates the need for the camera motion measuring device 104 to have an image processing function. The determination of the scanning motion from the geometric position relationship also allows a high precision measurement. Storing and specifying in terms of the coordinates on the CAD data makes it possible for the inspector to review inspection images of desired positions in an intuitive manner easily.

(Third Embodiment)

Figure 4:
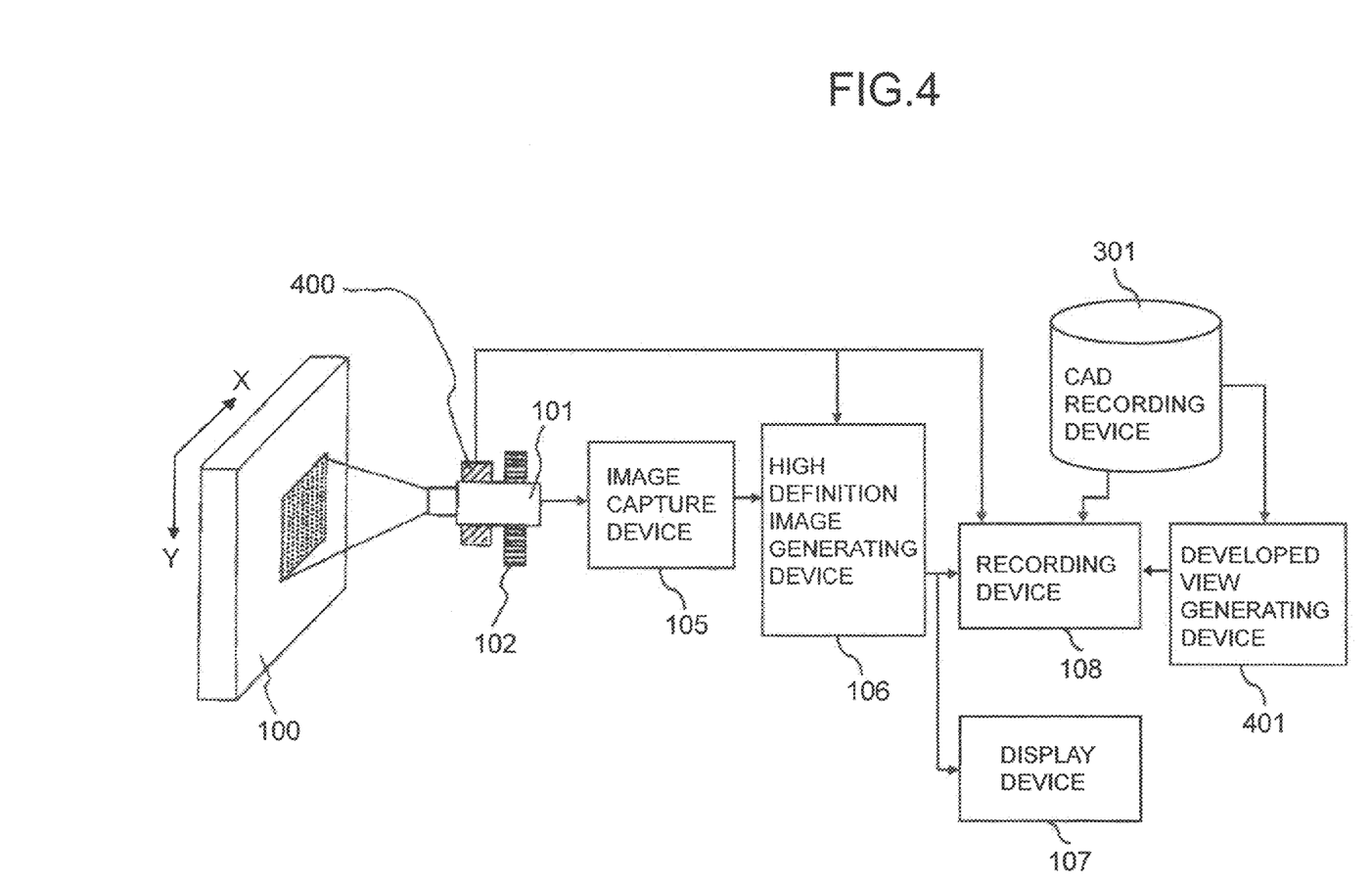
FIG. 4 is a block diagram of a visual inspection apparatus according to a third embodiment of the present invention.

FIG. 4 is a block diagram showing the configuration of a visual inspection apparatus according to a third embodiment of the present invention. In FIG. 4, identical or similar components to those of FIG. 1 will be designated by like reference numerals, and description thereof will be omitted. As compared to the first embodiment shown in FIG. 1, the third embodiment additionally includes a position measuring device 400, a developed view generating device 401, and a CAD recording device 301.

Next, the operation of the visual inspection apparatus according to the third embodiment will be described. The position measuring device 400 measures the scanning motion data on the TV camera by measuring the position and direction of the TV camera 101 with the use of a GPS (Global Positioning System) or other method, and transmits the scanning motion data to the recording device 108. The recording device 108 converts the measurements transmitted from the position measuring device 400 into coordinates on the CAD data that is recorded in the CAD recording device 301, and records and stores the coordinates. The developed view generating device 401 generates a developed view in which the inspection object 100 is developed in a plane from the CAD data of the CAD recording device 301, and transmits the developed view to the recording device 108. The developed view refers to a diagram into which the inspection object 100 is developed flatly, for example, when the inspection object 100 has a cylindrical surface. The recording device 108 generates a composite image in which a high definition image is superimposed on the developed view that is generated from the recorded position information on the inspection object 100. The composite image is displayed on the display device 107 and presented to the inspector.

According to the third embodiment, the direction and position of the TV camera are measured by the position measuring device 400, so that the accurate position can be recorded and stored into the recording device automatically. In addition, since the composite image in which a high definition image is superimposed on the developed view generated by the developed view generating device 401 is presented to the inspector, it is possible to easily create a sketch of defects, grasp the defects in view of the entire inspection object, and so on.

(Fourth Embodiment)

Figure 5:
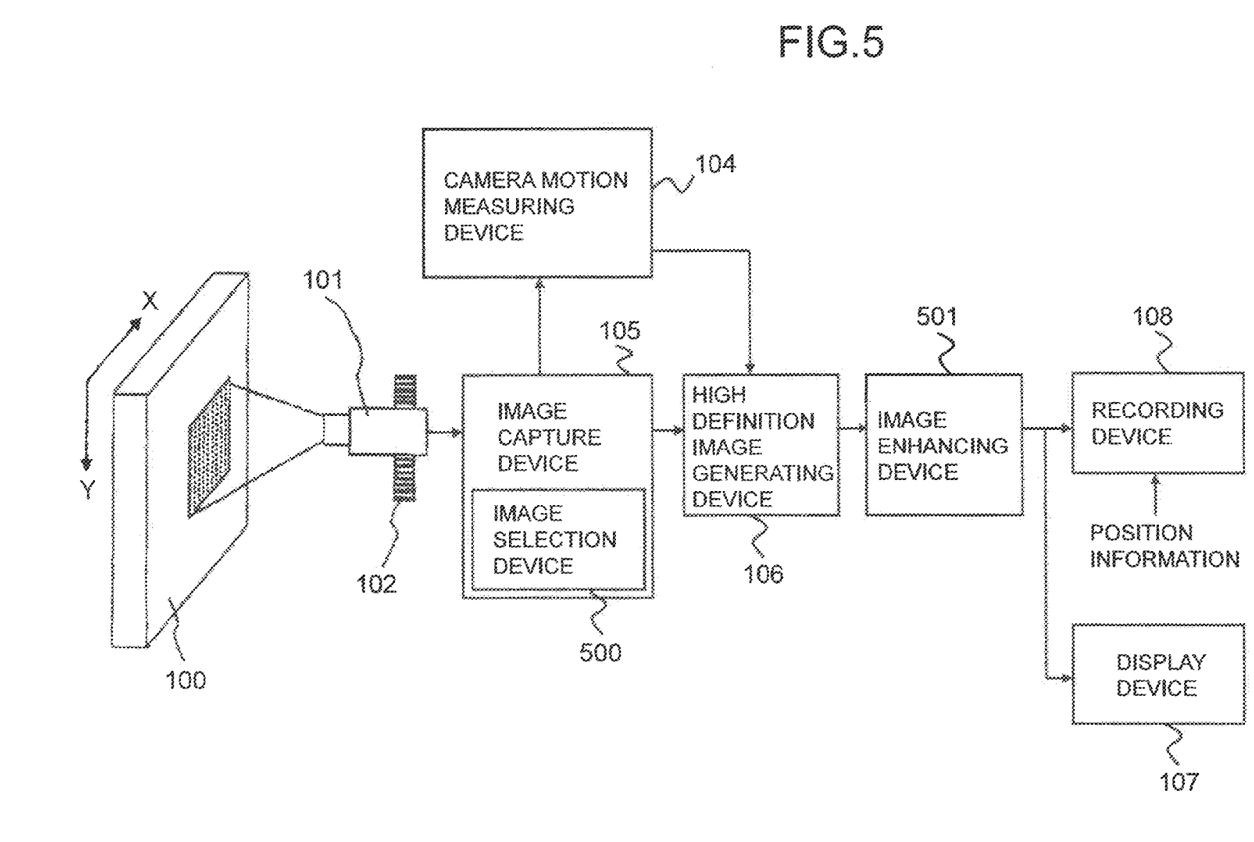
FIG. 5 is a block diagram of a visual inspection apparatus according to a fourth embodiment of the present invention.

FIG. 5 is a block diagram showing the configuration of a visual inspection apparatus according to a fourth embodiment of the present invention. In FIG. 5, identical or similar components to those of FIG. 1 will be designated by like reference numerals, and description thereof will be omitted. As compared to the first embodiment shown in FIG. 1, the fourth embodiment includes: an image selection device 500 which is added to the image capture device 105; and an image enhancing device 501.

Next, the operation of the visual inspection apparatus according to the fifth embodiment will be described. When the inspection object 100 is shot by the TV camera 101, the images can show sharp changes in brightness along the time axis when the ambient illumination or other environment is unstable. Moreover, if the scanning mechanism of the camera driving device 102 for producing the scanning motion of the TV camera 101 is unstable, the TV camera 101 can possibly make a sudden movement. If a high definition image is generated from the images of the TV camera 101 that are shot under such conditions, the quality of the high definition image will drop.

The fourth embodiment is intended to obtain a high definition image of stable quality even under such conditions. The image selection device 500 evaluates the image captured by the image capture device 105 for brightness changes over time, and determines not to output the image to the high definition image generating device 106 if a sharp change occurs in brightness. Along with the evaluation of brightness changes, the measurements of the camera motion measuring device 104 may also be evaluated to provide the function of detecting the occurrence of a sudden scanning motion and determining whether or not to make an output.

Another object of the present embodiment is to further improve the defect visibility. The image enhancing device 501 performs image processing pertaining to brightness enhancement such as edge enhancement on the high definition image. If there is any defect or the like, differences in brightness from the back ground become more noticeable, which improves the visibility of the defect.

According to the fourth embodiment, the image selection device determines whether or not to output images, so that high definition images of stable quality can be obtained even under such conditions that the ambient illumination and the scanning motion of the TV camera are unstable. The image enhancing device can perform brightness enhancement for improved defect visibility.

(Fifth Embodiment)

Figure 6:
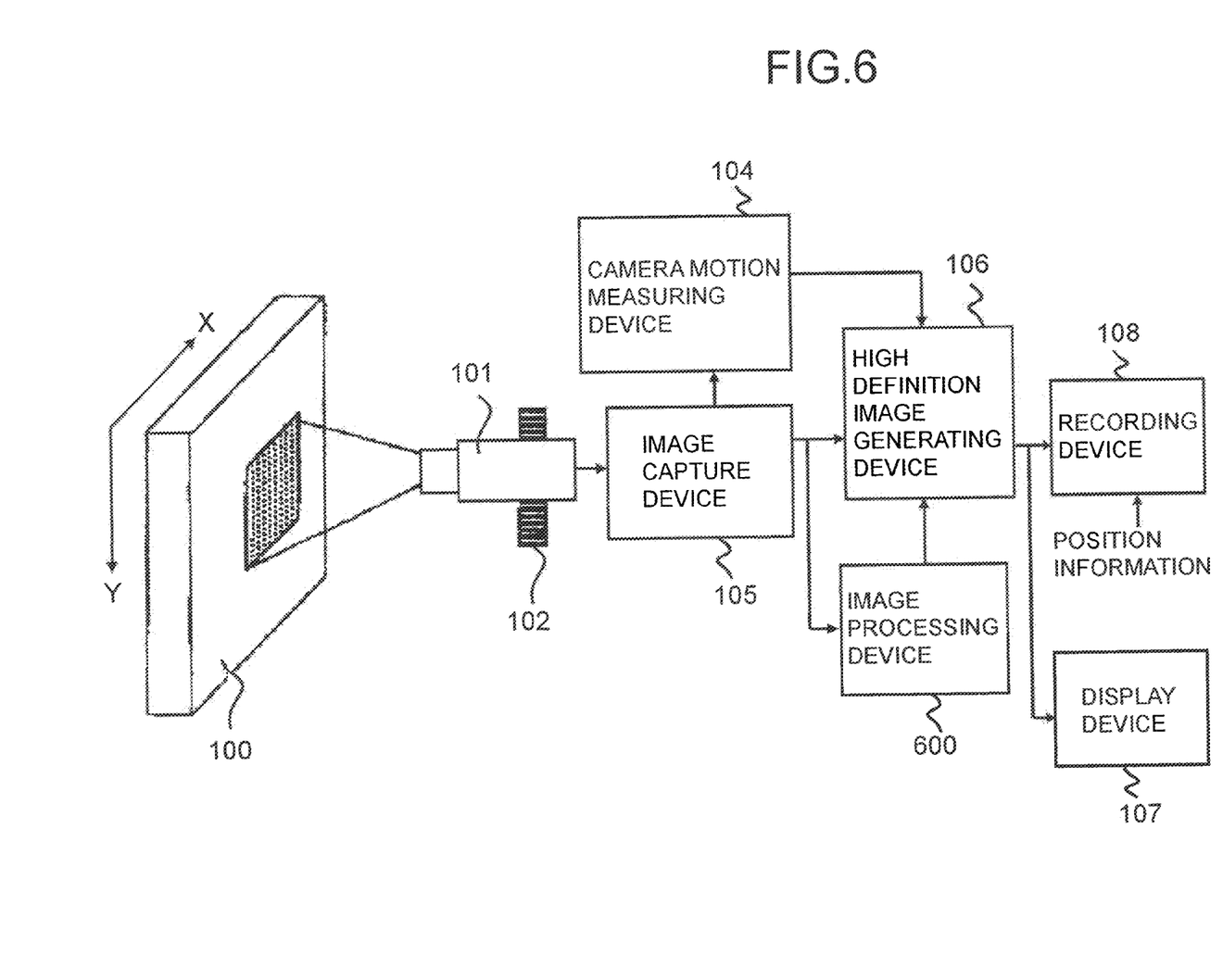
FIG. 6 is a block diagram of a visual inspection apparatus according to a fifth embodiment of the present invention.

FIG. 6 is a block diagram showing the configuration of a visual inspection apparatus according to a fifth embodiment of the present invention. In FIG. 6, identical or similar components to those of FIG. 1 will be designated by like reference numerals, and description thereof will be omitted. As compared to the first embodiment shown in FIG. 1, the fifth embodiment additionally includes an image processing device 600.

Next, the operation of the visual inspection apparatus according to the fifth embodiment will be described. The image captured by the image capture device 105 is transmitted to the image processing device 600. The image processing device 600 performs image processing to detect candidate areas where defects are estimated to exist. The high definition image generating device 106 generates a high definition image when a candidate area of a defect is detected by the image processing device 600.

According to the fifth embodiment, the amount of calculation for generating high definition images can be reduced to allow implementation with a low-priced computer for improved system economical efficiency. The amount of data to be stored and recorded can also be reduced for improved system economical efficiency.

(Sixth Embodiment)

Figure 7:
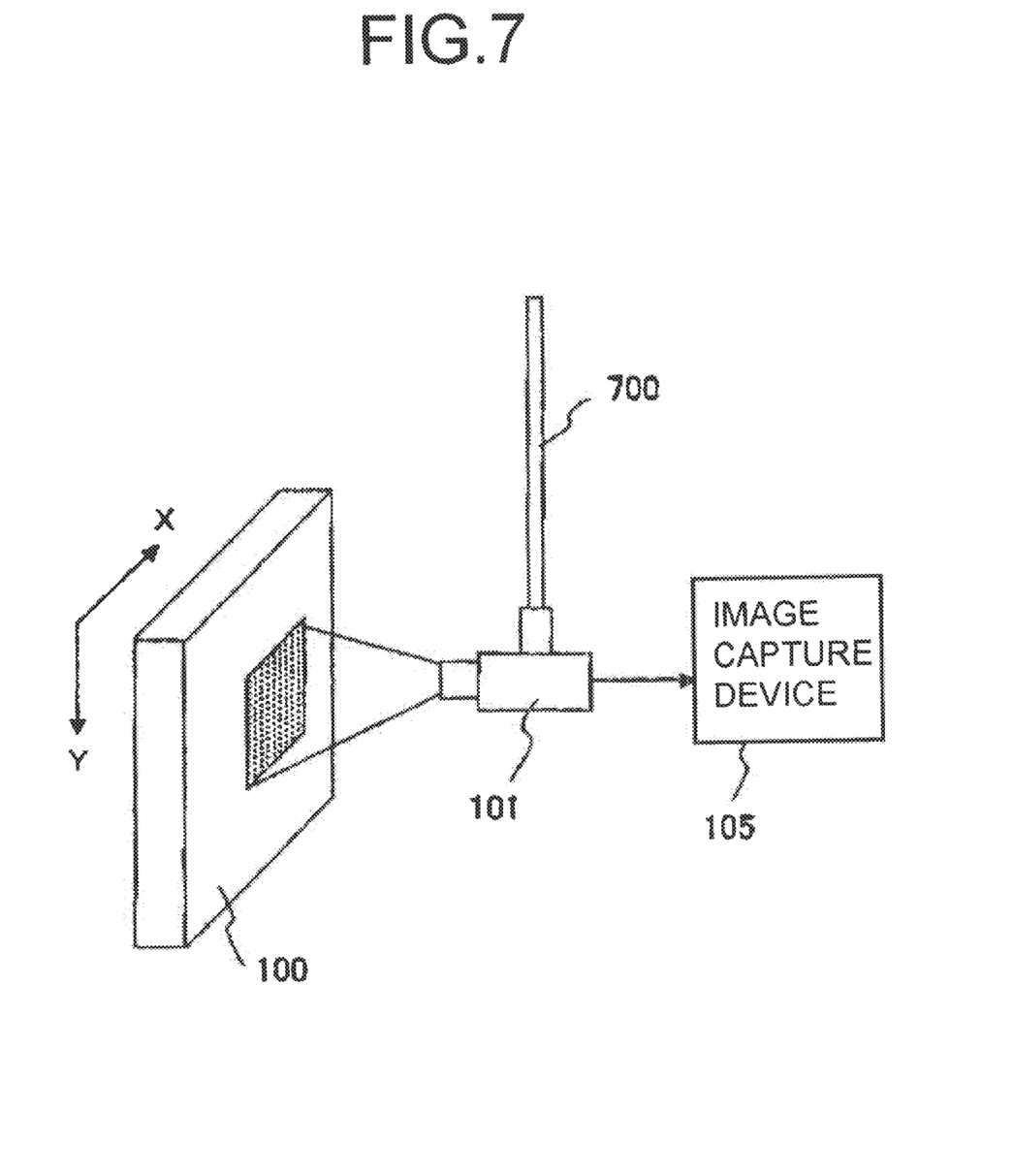
FIG. 7 is a block diagram of a visual inspection apparatus according to a sixth embodiment of the present invention.

FIG. 7 is a block diagram showing the configuration of a visual inspection apparatus according to a sixth embodiment of the present invention. FIG. 7 shows the TV camera 101 to the image capture device 105. The rest of the configuration is the same as in FIG. 1. As compared to the first embodiment shown in FIG. 1, the sixth embodiment includes a hanging tool 700 for hanging and supporting the TV camera instead of the camera driving device 102.

Next, the operation of the visual inspection apparatus according to the sixth embodiment will be described. The TV camera 101 is supported by a hanging tool 700 which is made of, for example, a hanging rod or the like attached to the top of the TV camera 101. An end of the hanging tool 700 opposite from the TV camera 101 is manipulated by the inspector or others so that the TV camera 101 makes a scanning motion over the inspection object 100.

According to the sixth embodiment, the same effects as those of the first embodiment can be obtained even with a jig that simply supports the TV camera, without the use of such machinery or mechanism as the camera driving device.

In a modification of the sixth embodiment, the hanging tool 700 may be omitted and an inspector may hold the TV camera 101 by hand and manually scan with the TV camera 101. In such a case, the scanning need not necessarily be performed intentionally since camera shakes in effect accomplish the same action as scanning and can thus be utilized for the same purpose.

(Other Embodiments)

The foregoing embodiments have been described solely by way of example, and the present invention is not limited thereto. For example, the features of the foregoing embodiments may be combined. For example, while the sixth embodiment introduces the hanging tool 700 by modifying the first embodiment in part, the hanging tool 700 may be combined with the second to fifth embodiments.

The foregoing embodiments have dealt with the cases where the inspection object 100 is a reactor internal structure of a nuclear power plant. The inspection object 100 is not limited thereto, however.

While the foregoing embodiments have dealt with the cases of driving the TV camera 101, it is only essential that the TV camera 101 and the inspection object 100 make a relative movement therebetween. The TV camera 101 may thus be fixed while the inspection object 100 is driven.

In the foregoing embodiments, the camera motion measuring device 104, the image capture device 105, the high definition image generating device 106, the display device 107, the recording device 108, the drive control device 300, the CAD recording device 301, the position measuring device 400, the developed view generating device 401, the image selection device 500, the image enhancing device 501, and the image processing device 600 have been described as "devices." These components need not necessarily be independent devices, however, and may be implemented by using one or a plurality of computers having such functions or using some of functions of a data processing apparatus.

The invention claimed is:

1. An appearance inspection apparatus comprising:
   an image capture unit that captures a picture of a TV camera as a digital image before and after the TV camera makes a relative scanning motion finer than pixels of the TV camera such that the TV camera moves relative to an inspection object;

a camera motion measuring unit that measures the relative scanning motion of the TV camera in the images with precisions of sub-pixels smaller than a single pixel;

a high definition image generating unit that generates a high definition image having a pixel resolution higher than that of the TV camera based on a plurality of the digital images captured by the image capture unit and scanning motion data on the TV camera measured by the camera motion measuring unit; and a recording unit that records and stores position information on the inspection object, wherein the high definition image generating unit calculates a relative position of the digital images in the high definition image by using the plurality of the digital images and the relative scanning motion of the TV camera, and estimates a brightness of each pixel of the high definition image by using each brightness of the digital images overlapping each other at each pixel of the high definition image.

2. The appearance inspection apparatus according to claim 1, further comprising:

a driving device that drives the TV camera so that the TV camera makes the relative scanning motion, wherein the TV camera shoots the inspection object.

3. The appearance inspection apparatus according to claim 1, further comprising:

a display unit that displays the high definition image.

4. The appearance inspection apparatus according to claim 1, wherein the driving device includes a hanging tool for hanging the TV camera.

5. The appearance inspection apparatus according to claim 1, wherein the camera motion measuring unit has an image processing means for measuring the relative scanning motion of the TV camera based on an output image of the image capture unit.

6. An appearance inspection apparatus comprising:

an image capture unit that captures a picture of a TV camera as a digital image before and after the TV camera makes a relative scanning motion finer than pixels of the TV camera such that the TV camera moves relative to an inspection object;

a camera motion measuring unit that measures the relative scanning motion of the TV camera in the images with precisions of sub-pixels smaller than a single pixel;

a CAD recording unit that contains CAD data describing a shape of the inspection object;

a high definition image generating unit that generates a high definition image having a pixel resolution higher than that of the TV camera based on a plurality of the digital images captured by the image capture unit and scanning motion data on the TV camera measured by the camera motion measuring unit; and a recording unit that records and stores position information on the inspection object, wherein the high definition image generating unit calculates a relative position of the digital images in the high definition image by using the plurality of the digital images and the relative scanning motion of the TV camera, and estimates a brightness of each pixel of the high definition image by using each brightness of the digital images overlapping each other at each pixel of the high definition image.

7. The appearance inspection apparatus according to claim 6, wherein the recording unit records and stores a position of the inspection object seen in the high definition image in terms of coordinates on the CAD data of the CAD recording unit, and can refer to the high definition image when the position of the inspection object is specified on the CAD data.

8. The appearance inspection apparatus according to claim 6, wherein the camera motion measuring unit includes a drive control unit for controlling the driving device, and measures the scanning motion of the TV camera based on control information of the drive control unit and the shape of the inspection object described by the CAD data of the CAD recording unit.

9. An appearance inspection apparatus comprising:

an image capture unit that captures a picture of a TV camera as a digital image before and after the TV camera makes a relative scanning motion finer than pixels of the TV camera such that the TV camera moves relative to an inspection object in the images with precisions of sub-pixels smaller than a single pixel;

a position measuring unit that measures scanning motion data on the TV camera based on a position and direction of the TV camera;

a recording unit that records the data measured by the position measuring unit;

a CAD recording unit that contains CAD data describing a shape of the inspection object;

a high definition image generating unit that generates a high definition image having a pixel resolution higher than that of the TV camera based on a plurality of the digital images captured by the image capture unit and the scanning motion data;

a developed view generating unit that generates a developed view in which the inspection object is developed in the plane; and a recording unit that records and stores position information on the inspection object, wherein the high definition image generating unit calculates a relative position of the digital images in the high definition image by using the plurality of the digital images and the relative scanning motion of the TV camera, and estimates a brightness of each pixel of the high definition image by using each brightness of the digital images overlapping each other at each pixel of the high definition image.

10. The appearance inspection apparatus according to claim 9, wherein the developed view generating unit generates the developed view of the inspection object based on the CAD data of the CAD recording unit; and the recording unit can generate a composite image in which the high definition image is superimposed on the developed view.

11. The appearance inspection apparatus according to claim 1, wherein the image capture unit includes an image selection unit that determines whether or not to output a captured image of the picture of the TV camera to the high definition image generating unit.

12. The appearance inspection apparatus according to claim 1, further comprising:

an image enhancing unit that performs brightness enhancing processing on the high definition image generated by the high definition image generating unit.

13. The appearance inspection apparatus according to claim 1, further comprising:

an image processing unit that detects a candidate area of a defect based on the picture of the TV camera, wherein the high definition image generating unit generates the high definition image when the defect candidate area is detected by the image processing unit.

14. An appearance inspection method comprising steps of:

shooting an inspection object with a TV camera while making the TV camera perform a relative scanning motion finer than pixels of the TV camera such that the TV camera moves relative to the inspection object;

capturing a picture shot by the TV camera into an image capture unit as a digital image;

measuring the scanning motion of the TV camera based on the image of the TV camera in the images with precisions of sub-pixels smaller than a single pixel;

generating, at a high definition image generating unit, a high definition image having a pixel resolution higher than that of the TV camera based on measurements of the scanning motion of the TV camera and the digital image captured into the image capture unit;

displaying the high definition image; and recording and storing position information on the inspection object, wherein the high definition image generating unit calculates a relative position of the digital images in the high definition image by using the plurality of the digital images and the relative scanning motion of the TV camera, and estimates a brightness of each pixel of the high definition image by using each brightness of the digital images overlapping each other at each pixel of the high definition image.

* * * * *